United States Patent
Yu et al.

(10) Patent No.: US 11,952,341 B2
(45) Date of Patent: Apr. 9, 2024

(54) METHOD OF PREPARING HIGH CHIRAL PURITY LACTAM INTERMEDIATE AND BRIVARACETAM

(71) Applicants: YANGZHOU AORUITE PHARMACEUTICAL CO. LTD., Jiangsu (CN); YANGZHOU LIANAO BIOMEDICAL CO., LTD., Jiangsu (CN)

(72) Inventors: Zhenpeng Yu, Jiangsu (CN); Fei Xiao, Jiangsu (CN); Guoping Wang, Jiangsu (CN); Shuxian Qi, Jiangsu (CN); He Gao, Jiangsu (CN)

(73) Assignees: YANGZHOU AORUITE PHARMACEUTICAL CO., LTD., Jiangsu (CN); YANGZHOU LIANAO BIOMEDICAL CO., LTD., Jiangsu (CN)

( * ) Notice: Subject to any disclaimer, the term of this patent is extended or adjusted under 35 U.S.C. 154(b) by 910 days.

(21) Appl. No.: 17/059,125

(22) PCT Filed: Dec. 17, 2018

(86) PCT No.: PCT/CN2018/121624
§ 371 (c)(1),
(2) Date: Nov. 25, 2020

(87) PCT Pub. No.: WO2019/157856
PCT Pub. Date: Aug. 22, 2019

(65) Prior Publication Data
US 2023/0066606 A1    Mar. 2, 2023

(30) Foreign Application Priority Data

Feb. 13, 2018 (CN) .......................... 201810148128.0
Dec. 3, 2018 (CN) .......................... 201811465520.4

(51) Int. Cl.
*C07D 207/27* (2006.01)

(52) U.S. Cl.
CPC ........ *C07D 207/27* (2013.01); *C07B 2200/07* (2013.01)

(58) Field of Classification Search
CPC .................................................... C07D 207/27
See application file for complete search history.

(56) References Cited

U.S. PATENT DOCUMENTS

2008/0009638 A1    1/2008  Yves et al.

FOREIGN PATENT DOCUMENTS

| CN | 101263113 | A | 9/2008 | |
| CN | 104892483 | A | 9/2015 | |
| CN | 106748950 | A | 5/2017 | |
| CN | 107513031 | * | 12/2017 | ........... C07D 207/27 |
| CN | 107513031 | A | 12/2017 | |
| CN | 108101823 | A | 6/2018 | |
| CN | 108101824 | A | 6/2018 | |
| WO | 2017/076737 | A1 | 5/2017 | |
| WO | 2017/076738 | A1 | 5/2017 | |

* cited by examiner

*Primary Examiner* — Irina Neagu
(74) *Attorney, Agent, or Firm* — NKL Law; Allen Xue

(57) ABSTRACT

The invention discloses a method of preparing a high chiral purity lactam intermediate D comprising a step of reducing a compound C to lactam intermediate D in a solvent by hydrogenation reduction using a heavy metal catalyst and a chiral inducer. Brivaracetam can be prepared in a single step using the lactam intermediate D. The synthesis route is short, reaction conditions are mild, post-treatment is simple, reaction yield is high, chiral selectivity is good, and production cost is low. The conversion rate of the compound C in the reaction is 81%, and the DE value of the compound D is more than 99.0%, which is suitable for industrial production.

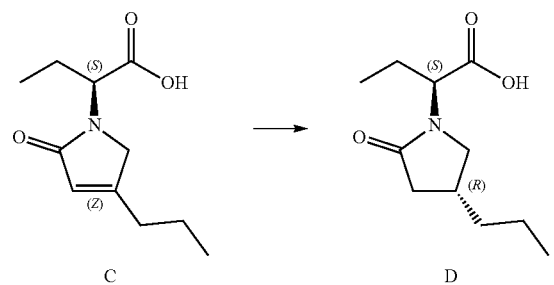

8 Claims, No Drawings

METHOD OF PREPARING HIGH CHIRAL PURITY LACTAM INTERMEDIATE AND BRIVARACETAM

TECHNICAL FIELD

The present invention relates to the field of organic synthesis. Specifically, the invention provides a method of preparing a high chiral purity lactam intermediate.

BACKGROUND

The invention discloses a method of preparing a high chiral purity lactam intermediate and brivaracetam. The invention provides a method of preparing a lactam intermediate compound represented by molecular formula D, which comprises a step of reducing a compound C to a lactam intermediate D in a solvent by hydrogenation reduction using a heavy metal catalyst and a chiral inducer. Brivaracetam can be prepared in a single step using the lactam intermediate compound represented by molecular formula D of the present invention. The synthesis route is short, reaction conditions are mild, post-treatment is simple, reaction yield is high, chiral selectivity is good, and production cost is low. The conversion rate of the compound C in the reaction is 81%, and the de value of the compound D is more than 99.0%, which is suitable for industrial production.

SUMMARY OF THE INVENTION

The purpose of the present application is to provide a method of preparing a high chiral purity lactam intermediate.

To achieve the aforementioned purpose of the invention, the following technical solutions are used in the invention for preparation of high chiral purity lactam intermediate:

A method of preparing a lactam intermediate compound of formula D, wherein a compound of formula C in solvent is reduced by hydrogenation reduction using a heavy metal catalyst and a chiral inducer, thereby obtaining the lactam intermediate compound of formula D.

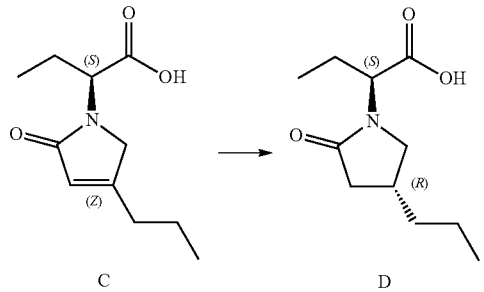

Further, the solvent is selected from water, methanol, ethanol, isopropanol, propanol, butanol, isobutanol, acetone, tetrahydrofuran, acetonitrile, and a mixture thereof. Preferably, the solvent is ethanol.

Further, the heavy metal catalyst is selected from palladium carbon, palladium, platinum carbon, platinum, ruthenium carbon, rhodium carbon, palladium alumina, palladium silica, palladium barium carbonate, palladium calcium carbonate, palladium carbon hydroxide, palladium dioxide; and preferably, is palladium carbon.

Further, the chiral inducer is formic acid, citric acid, malonic acid, succinic acid, 1,3,5-triazine-2,4,6-trithione trisodium salt (CAS 17766-26-6) hydrochloric acid, hydrobromic acid, or a mixture thereof, and preferably, is hydrobromic acid.

Further, the ratio of the mass of the chiral inducer to that of the compound is at most 5. Preferably, the ratio of the mass of the chiral inducer to that of compound C is at most 3, and more preferably, the ratio of the mass of the chiral inducer to that of compound C is at most 1.

Further, the pressure of hydrogen is at most 5 bar, and the reaction temperature is −20 to 50° C., preferably −10 to 0° C.

Another purpose of the present invention is to provide a method for preparing brivaracetam.

To achieve the aforementioned purpose of the invention, the following technical solutions are used in the invention for the preparing method of brivaracetam.

The invention provides a method for preparing brivaracetam, which comprises the steps of: obtaining the lactam intermediate compound of formula D by the method mentioned hereinabove, and mixing the compound of formula D with solvent, adding an activator, and reacting by introducing ammonia gas, thereby obtaining the brivaracetam.

Further, the activator is thionyl chloride, oxalyl chloride, phosphorus oxychloride, methanesulfonyl chloride, pivaloyl chloride, isobutyl chloroformate, and preferably pivaloyl chloride. The solvent is halogenated alkanes; and the reaction temperature is −20 to 30° C., and preferably −10 to 0° C. If the activator is replaced with HATU, HBTU and etc., the reaction status is good but there are some residues of HOAT and HOBT which are difficult to be removed.

Compared with the prior art, the beneficial effects of the present invention comprises:

1. In the preparation, it is unnecessary to use a chiral chromatography column to isolate the isomers, and the effective component can be isolated just by the steps of extraction, wash and dry, and concentration. The isolation process is simple and low cost.

2. The reaction intermediate is solid and easy to be further purified by recrystallization.

3. There is no high temperature and high pressure reaction during the synthesis. The operation is simple and safe.

4. By adding the chiral inducer during the reaction, the selectivity of diastereomer is greatly improved, the conversion rate of raw materials is doubled compared to the rate of the conventional reduction method, and the use of expensive uncommon additives is avoided.

5. The de value of intermediate synthetized by the present method is more than 99.0%, so that only simple recrystallization is required to meet the isomorphic control requirements of API.

DETAILED DESCRIPTION OF THE INVENTION

In the following, the present invention will be further described in combination with specific embodiments. It should be understood that these embodiments are only used to illustrate the present invention, but not to limit the scope of the present invention. After reading the present invention, all the modifications that equivalents to the present invention by those skilled in the art fall within the scope defined by the appended claims of this application.

Example 1

Preparation of Compound D

To a 1 L four-necked reaction flask were added citric acid monohydrate (50 g 0.237 mol), and water 500 ml. After stirring till dissolve, 5% Palladium carbon (0.5 g) was added. After stirring, the compound of formula C 50 g (0.237 mol) was added, and the temperature was maintained at 30° C. The air was replaced with hydrogen wherein hydrogen pressure was 2 ba, and reaction was conducted under stirring. After reacting for 20 hours, TLC monitoring showed that the raw materials were consumed completely, and the reaction was stopped. The reaction mixture was filtered, adjusted to PH=2 with 2M hydrochloric acid, cooled to 5° C., filtered, and washed with 50 ml water to obtain a white solid (46 g), which was recrystallized using 100 ml of methyl tert-butyl ether to obtain a white solid (41 g, 0.192 mol). Yield 81%, HPLC 99.52%, de % 99.2%.

Example 2

Preparation of Compound D

To a 1 L four-necked reaction flask were added malonic acid 12 g (0.115 mol), water 250 ml, and isopropanol 250 ml. After stirring till dissolve, 10% Palladium carbon 0.5 g was added. After stirring, the compound of formula C 50 g (0.237 mol) was added, and the temperature was maintained at 30° C. The air was replaced with hydrogen wherein the hydrogen pressure was 4 ba, and reaction was conducted under stirring. After reacting for 20 hours, TLC monitoring showed that the raw materials were consumed completely, and the reaction was stopped. The reaction mixture was filtered, adjusted to PH=2 with 2M hydrochloric acid, cooled to 5° C., filtered, and washed with 50 ml water. The crude product was recrystallized using 100 ml of methyl tert-butyl ether to obtain a white solid (44 g, 0.206 mol). Yield 81%, HPLC 99.23%, de % 99.0%.

Example 3

Preparation of Compound D

To a 500 ml reactor were added citric acid monohydrate 20 g (0.095 mol), and water 100 ml. After stirring till dissolve, 10% Palladium carbon 0.5 g, 1,3,5-triazine-2,4,6-trithione trisodium salt 0.0001 g was added and stirred. Then the compound of formula C 10 g (0.047 mol) was added, and the temperature was maintained at 5° C. The air was replaced with hydrogen and the hydrogen pressure was 5 ba, and reaction was conducted under stirring. After reacting for 20 hours, TLC monitoring showed that the raw materials were consumed completely, and the reaction was stopped. The reaction mixture was filtered, adjusted to PH=2 with 2M hydrochloric acid, cooled to 5° C., filtered, and washed with 20 ml water. The crude was recrystallized using 20 ml of methyl tert-butyl ether to obtain a white solid (8.1 g, 0.038 mol). Yield 82%, HPLC 95.6%, de % 99.1%.

Example 4

Preparation of Compound D

To a 500 ml reactor were added malonic acid 9.8 g (0.094 mol), water (100 ml) and isopropanol (100 ml). After stirring till dissolve, 10% Palladium carbon (10 g) was added. After stirring, the compound of formula C (20 g, 0.094 mol) was added, and the temperature was maintained at −10° C. The air was replaced with hydrogen and the hydrogen pressure was 1 ba, and reaction was conducted under stirring. After reacting for 25 hours, TLC monitoring showed that the raw materials were consumed completely, and the reaction was stopped. The organic solvent was removed at 40° C. using rotary evaporation, and the reaction mixture was filtered, adjusted to PH=2 with 2M hydrochloric acid, cooled to 5° C., filtered, and washed with 20 ml water. The crude was recrystallized using 40 ml of methyl tert-butyl ether to obtain a white solid (17 g, 0.079 mol). Yield 86%, HPLC 86.2%, de % 99.0%.

Example 5

Preparation of Compound D

To a 500 ml four-necked reaction flask were added methanoic acid 1.1 g (0.024 mol), water 100 ml, and isopropanol 100 ml. After stirring till dissolve, 5% platinum carbon 0.25 g, 1,3,5-triazine-2,4,6-trithione trisodium salt 0.0001 g were added and stirred. The compound of formula C (10 g, 0.047 mol) was added, and the temperature was maintained at −20° C. The air was replaced with hydrogen wherein the hydrogen pressure was 5 ba, and reaction was conducted under stirring. After reacting for 32 hours, TLC monitoring showed that the raw materials were consumed completely, and the reaction was stopped. The reaction mixture was filtered, adjusted to PH=2 with 2M hydrochloric acid, cooled to 5° C., filtered, and washed with 10 ml water. The crude product was recrystallized using 20 ml of methyl tert-butyl ether to obtain a white solid (8.5 g, 0.040 mol). Yield 85%, HPLC 93.1%, de % 99.5%.

Example 6

Preparation of Compound D

To a 500 ml reactor were added succinic acid 22.2 g (0.188 mol), water 200 ml, and isopropanol 100 ml. After stirring till dissolve, 10% Palladium carbon 0.5 g, 1,3,5-triazine-2,4,6-trithione trisodium salt 0.01 g were added and stirred. The compound of formula C 20 g (0.094 mol) was added, and the temperature was maintained at −20° C. The air was replaced with hydrogen wherein the hydrogen pressure was 5 ba, and reaction was conducted under stirring. After reacting for 40 hours, TLC monitoring showed that the raw materials were consumed completely, and the reaction was stopped. The reaction mixture was filtered, and the organic solvent was removed at 40° C. using rotary evaporation, and mixture was adjusted to PH=2 with 2 M hydrochloric acid, cooled to 5° C., filtered, and washed with 20 ml water. The crude was recrystallized using 40 ml of methyl tert-butyl ether to a obtain white solid (15.7 g, 0.074 mol). Yield 79%, HPLC 93.3%, de % 99.1%.

Example 7

Preparation of Compound D

To a 500 ml reactor were added citric acid monohydrate 5 g (0.0238 mol), and methanol 300 ml. After stirring till dissolve, 10% palladium carbon 2.5 g was added. After stirring, 1,3,5-Triazine-2,4,6-trithione trisodium salt 0.0005 g was added and stirred. The compound of formula C 50 g (0.237 mol) was added, and the temperature was maintained at −10° C. The air was replaced with hydrogen wherein the hydrogen pressure was 5 ba, and reaction was conducted under stirring. After reacting for 30 hours, TLC monitoring showed that the raw materials were consumed completely, and the reaction was stopped. The reaction mixture was filtered, the solvent was removed at 40° C. using rotary evaporation. To the evaporated residue was added 200 ml water, and mixture was extracted with 200 ml ethyl acetate extraction. The ethyl acetate phase was extracted with 200 ml of 1M sodium hydroxide aqueous solution, and aqueous phase was adjusted to pH=2 using 6 M hydrochloric acid at 10-20° C., cooled to 5° C., and white solids were precipitated and filtered. The crude product was recrystallized using 100 ml of methyl tert-butyl ether to obtain a white solids (39 g, 0.183 mol). Yield 77%, HPLC 97.65%, de % 99.2%.

Example 8

Under the Protection of nitrogen, to a 250 ml reaction flask, anhydrous ethanol 150 ml, and 5% palladium carbon 1.5 g were added and stirred. 5 ml of 1M hydrochloric acid solution was added, stirred for 30 min, and cooled to −10° C. The compound of formula C (15 g, 0.071 mol) was added. The air was replaced with hydrogen wherein the hydrogen pressure was 2 ba, and reaction was conducted under stirring. After 20 hours, a sample was taken and HPLC monitoring showed that reaction was conducted completely, and the reaction was stopped. The catalyst was separated by filtration (which was recovered for use), the solvent was removed using rotary evaporation, and white solids were precipitated, and recrystallized using the mixture of methyl tert-butyl ether:cyclohexane=30 ml: 150 ml, to obtain the product (13.4 g, 0.063 mol). Yield: 88.7%, de % 99.1%.

Example 9

Under the Protection of nitrogen, to a 250 ml reaction flask, anhydrous ethanol 150 ml, and 5% palladium carbon 1.5 g were added and stirred. 5 ml of 3 M hydrochloric acid solution was added, stirred for 30 min, and cooled to −10° C. The compound of formula C (15 g, 0.071 mol) was added. The air was replaced with hydrogen wherein the hydrogen pressure was 2 ba, and reaction was conducted under stirring. After 20 hours, a sample was taken, HPLC monitoring showed that reaction was conducted completely, and the reaction was stopped. The catalyst was separated by filtration (which was recovered for use), the solvent was removed using rotary evaporation, white solids was precipitated, and 13.2 g (0.062 mol) of the product was obtained by recrystallized using the mixture of methyl tert-butyl ether:cyclohexane=30 ml: 150 ml. Yield: 87.3%, de % 99.1%.

Example 10

Under the Protection of nitrogen, to a 250 ml reaction flask, anhydrous ethanol 150 ml, and 5% palladium carbon 0.75 g were added and stirred. 5 ml of 1 M hydrobromic acid solution was added, stirred for 30 min, cooled to −10° C. The compound of formula C (15 g, 0.071 mol) was added. The air was replaced with hydrogen wherein the hydrogen pressure was 2 ba, and reaction was conducted under stirring. After 20 hours, a sample was taken, HPLC monitoring showed that reaction was conducted completely, and the reaction was stopped. The catalyst was separated by filtration (which was recovered for use), the solvent was removed using rotary evaporation, white solids was precipitated, and 14.2 g (0.067 mol) of the product was obtained by recrystallized using the mixture of methyl tert-butyl ether:cyclohexane=30 ml:150 ml. Yield: 94.4%, de % 99.3%.

Example 11

Under the Protection of nitrogen, to a 250 ml reaction flask, anhydrous ethanol 150 ml and 5% palladium carbon (which was recovered and re-used once) 1.5 g were added and stirred. 5 ml of 1 M hydrobromic acid solution was added, stirred for 30 min, cooled to −20° C. The compound of formula C (15 g, 0.071 mol) was added. The air was replaced with hydrogen wherein the hydrogen pressure was 5 ba, and reaction was conducted under stirring. After 10 hours, a sample was taken, HPLC monitoring showed that reaction was conducted completely, and the reaction was stopped. The catalyst was separated by filtration (which was recovered for use), the solvent was removed using rotary evaporation, white solids were precipitated, and 14.3 g (0.067 mol) of the product was obtained by recrystallized using methyl tert-butyl ether. Yield: 94.4%, de % 99.4%.

Example 12

Under the Protection of nitrogen, to a 250 ml reaction flask, anhydrous ethanol 150 ml, and 5% palladium carbon (which was recovered and re-used once) 1.5 g were added, and stirred. 5 ml of 2 M hydrobromic acid solution was added, stirred for 30 min, cooled to −20° C. The compound of formula C (15 g, 0.071 mol) was added. The air was replaced with hydrogen wherein the hydrogen pressure was 2 ba, and reaction was conducted under stirring. After 20 hours, a sample was taken, HPLC monitoring showed that reaction was conducted completely, and the reaction was stopped. The catalyst was separated by filtration (which was recovered for use), the solvent was removed using rotary evaporation, white solids was precipitated, and 14.0 g (0.066 mol) of the product was obtained by recrystallized using the mixture of methyl tert-butyl ether:cyclohexane=30 ml:150 ml. Yield: 93.0%, de % 99.2%.

Example 13

Under the Protection of nitrogen, to a 250 ml reaction flask, anhydrous ethanol 150 ml, and 5% palladium carbon 1.5 g were added and stirred. 5 ml of 1 M hydrochloric acid solution was added, stirred for 30 min, cooled to −10° C. The compound of formula C 15 g (0.071 mol) was added. The air was replaced with hydrogen wherein the hydrogen pressure was 5 ba, and reaction was conducted under stirring. After 8 hours, a sample was taken, HPLC monitoring showed that reaction was conducted completely, and the reaction was stopped. The catalyst was separated by filtration, the solvent was removed using rotary evaporation, white solids was precipitated, and 13.4 g (0.063 mol) of the product was obtained by recrystallized using the mixture of methyl tert-butyl ether:cyclohexane=30 ml:150 ml. Yield: 88.7%, de % 89.6%.

Example 14

Under the Protection of nitrogen, to a 250 ml reaction flask, anhydrous ethanol 150 ml, and 10% palladium carbon 1.5 g were added and stirred. 5 ml of 1 M HBr solution was added, stirred for 30 min, cooled to −5° C. The compound of formula C 15 g (0.071 mol) was added. The air was replaced with hydrogen wherein the hydrogen pressure was 2 ba, and reaction was conducted under stirring. After 20 hours, a sample was taken, HPLC monitoring showed that reaction was conducted completely, and the reaction was stopped. The catalyst was separated by filtration, the solvent was removed using rotary evaporation, white solids was precipitated, and 14.2 g (0.067 mol) of the product was obtained by recrystallized using the mixture of methyl tert-butyl ether:cyclohexane=30 ml:150 ml. Yield: 94.4%, de % 99.3%.

Example 15

Under the Protection of nitrogen, to a 100 L reactor, 95% ethanol 60 L, 5% ruthenium carbon 300 g were added and stirred. 1 L of 1 M HBr solution was added, stirred for 30 min, cooled to 0° C. The compound of formula C (6 kg, 28.4 mol) was added and stirred for 1 h. The air was replaced with hydrogen wherein the hydrogen pressure was 2 ba, and reaction was conducted under stirring. After 20 hours, a sample was taken, HPLC monitoring showed that reaction was conducted completely, and the reaction was stopped. The catalyst was removed by filtration, the solvent was removed using rotary evaporation, white solids was precipitated, and 5.8 kg (27.2 mol) of the product was obtained by recrystallized using the mixture of methyl tert-butyl ether:cyclohexane=12 L:60 L. Yield: 95.8%, de % 99.0%.

Example 16

Preparation of Brivaracetam

To 500 ml reaction flask, compound D 40 g (0.188 mol), and dichloromethane 240 ml were added and stirred till dissolve. The reaction temperature was maintained at 0° C., and methanesulfonyl chloride 22 g (0.192 ml) was added dropwise. After completing the addition, the reaction was stirred for 30 min, and ammonia gas (1-3 bar) was introduced. The reaction was monitored by TLC. After 6 hours, the reaction was completed and the introduction of ammonia gas was stopped. The reaction liquid was suction filtered under reduced pressure, washed by adding 100 ml water (×2). The dichloromethane phase was separated, and dichloromethane was removed by rotary evaporation. Into the evaporated residue, isopropyl acetate (60 ml) was added, and heated till dissolve. The solution was crystallized by cooling to 0-5° C., suction filtered. After drying, pure Brivaracetam (32 g) 0.151 mol was obtained. Chemical purity 99.8%, optical purity 99.6%.

Example 17

Preparation of Brivaracetam

To 500 ml reaction flask, compound D 44 g (0.206 mol), and dichloromethane 264 ml were added and stirred till dissolve. The reaction temperature was maintained at 0° C., and methanesulfonyl chloride 23.6 g (0.206 ml) was added dropwise. After completing the addition, the reaction was stirred for 30 min, and ammonia gas (1-3 ba) was introduced. The reaction was monitored by TLC. After 6 hours, the reaction was completed and the introduction of ammonia gas was stopped. The reaction liquid was suction filtered under reduced pressure, washed by adding 100 ml water (×2). The dichloromethane phase was separated, and dichloromethane was removed by rotary evaporation. Into the evaporated residue, isopropyl acetate 60 ml was added, and heated till dissolve. The solution was crystallized by cooling to 0-5° C., suction filtered. After drying, pure Brivaracetam (33 g) 0.155 mol was obtained. Chemical purity 99.6%, optical purity 99.5%.

Example 18

Under the protection of nitrogen, to 500 ml reaction flask, 100 g compound D (0.47 mol), and dichloromethane 1 L were added and stirred till dissolve. The reaction temperature was maintained at 0° C., and 95 g triethylamine was added. Pivaloyl chloride 113 g was added dropwise while the temperature was maintained at 0-5° C. After addition, the reaction mixture was stirred for 1 hour, sampled, and monitored by HPLC until the completion of the reaction. The ammonia gas was slowly introduced and a large amount of white solids were precipitated in the reaction flask. PH was controlled >7, a sample was taken and monitored by HPLC until the completion of the reaction. The introduction of ammonia gas was stopped. The solids precipitated in the solution were removed by filtration. Into the dichloromethane phase was added 500 ml deionized water at 5° C., PH was adjusted to neutral with 0.5 M aqueous hydrochloric acid solution at 5° C., and the dichloromethane phase was separated. The water phase was extracted once with dichloromethane. The dichloromethane phases were combined, and solvent was removed by rotary evaporation. The recrystallization was conducted once by using a mixture of isopropyl ether:cyclohexane (200 ml:1000 ml) to obtain a white solid 84 g (0.40 mol). Yield 85.1%, de %: 99.2%.

Example 19

Under the protection of nitrogen, 5 kg compound D and dichloromethane 50 L were added into 100 L reaction flask, and stirred till dissolve. The reaction temperature was maintained at 0° C., and 5.7 kg triethylamine was added. Pivaloyl chloride 6.78 kg was added dropwise while the temperature was maintained at 0-5° C. After addition, the reaction mixture was stirred for 1 hour, sampled, monitored by HPLC until the completion of the reaction. The ammonia gas was slowly introduced and a large amount of white solids were precipitated in the reaction flask. PH was controlled >7, a sample was taken and monitored by HPLC until the completion of the reaction. The introduction of ammonia gas was stopped. The solids precipitated in the solution were removed by filtration. Into the dichloromethane phase was added 30 L deionized water at 5° C., PH was adjusted to neutral with 0.5 M aqueous hydrochloric acid solution at 5° C., and the dichloromethane phase was separated. The water phase was extracted once with dichloromethane. The dichloromethane phases were combined, and the solvent was removed by rotary evaporation. The recrystallization was conducted once using the mixture of isopropyl ether:cyclohexane (10 L:50 L) to obtain a white solid 4.5 kg. Yield 90.0%, de %: 99.1%.

The invention claimed is:

1. A method for preparing a lactam intermediate compound of formula D, which comprises:

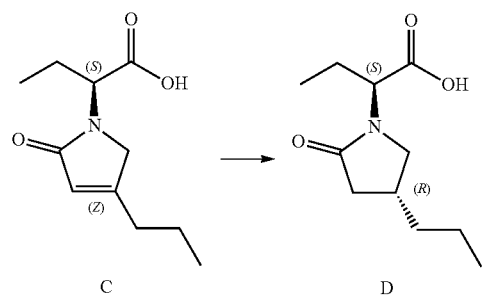

reducing a compound of formula C in a solvent by hydrogenation reduction using a heavy metal catalyst and a chiral inducer, thereby obtaining the lactam intermediate compound of formula D;
wherein the heavy metal catalyst is selected from the group consisting of palladium carbon, platinum carbon, ruthenium carbon, and rhodium carbon; and
the chiral inducer is hydrochloric acid, hydrobromic acid, or a mixture thereof.

2. The method of claim 1, wherein the solvent is selected from the group consisting of water, methanol, ethanol, isopropanol, propanol, butanol, isobutanol, acetone, tetrahydrofuran, acetonitrile, and a combination thereof.

3. The method of claim 1, wherein the ratio of the mass of the chiral inducer to the mass of compound C is at most 5.

4. The method of claim 1, wherein hydrogen has a pressure of at most 5 bar.

5. The method of claim 1, wherein the reducing temperature is −20° C. to 50° C.

6. A method for preparing brivaracetam, which comprises the steps of:
preparing the lactam intermediate compound of formula D by the method of claim 1; and mixing the lactam intermediate compound of formula D with a solvent, adding an activator, and reacting with ammonia gas, thereby obtaining brivaracetam.

7. The preparation method according to claim 6, wherein the activator is selected from the group consisting of thionyl chloride, oxalyl chloride, phosphorus oxychloride, methanesulfonyl chloride, pivaloyl chloride, and isobutyl chloroformate;
the solvent is halogenated alkanes; and
the reaction temperature is −20 to 30° C.

8. The method of claim 1, wherein the solvent is selected from water, ethanol, and a combination thereof.

* * * * *